United States Patent
Yin

(10) Patent No.: US 11,755,225 B2
(45) Date of Patent: Sep. 12, 2023

(54) SYSTEMS AND METHODS FOR DATA STORAGE

(71) Applicant: SHANGHAI UNITED IMAGING HEALTHCARE CO., LTD., Shanghai (CN)

(72) Inventor: Gang Yin, Shanghai (CN)

(73) Assignee: SHANGHAI UNITED IMAGING HEALTHCARE CO., LTD, Shanghai (CN)

( * ) Notice: Subject to any disclaimer, the term of this patent is extended or adjusted under 35 U.S.C. 154(b) by 106 days.

(21) Appl. No.: 17/010,845

(22) Filed: Sep. 3, 2020

(65) Prior Publication Data

US 2020/0401338 A1    Dec. 24, 2020

(30) Foreign Application Priority Data

Sep. 3, 2019    (CN) .......................... 201910827536.3

(51) Int. Cl.
*G06F 3/06* (2006.01)

(52) U.S. Cl.
CPC .......... *G06F 3/0647* (2013.01); *G06F 3/0619* (2013.01); *G06F 3/0652* (2013.01); *G06F 3/0683* (2013.01)

(58) Field of Classification Search
CPC .... G06F 3/0647; G06F 3/0619; G06F 3/0652; G06F 3/0683; G06F 3/0608;
(Continued)

(56) References Cited

U.S. PATENT DOCUMENTS

| 2004/0130750 A1 | 7/2004 | Ushida et al. |
| 2006/0290998 A1 | 12/2006 | Jung et al. |

(Continued)

FOREIGN PATENT DOCUMENTS

| CN | 103455284 A | 12/2013 |
| CN | 104731858 A | 6/2015 |

(Continued)

OTHER PUBLICATIONS

First Office Action in Chinese Application No. 201910827536.3 dated Sep. 1, 2021, 17 pages.

(Continued)

*Primary Examiner* — Jason W Blust
(74) *Attorney, Agent, or Firm* — METIS IP LLC

(57) ABSTRACT

The present disclosure relates to systems and methods for data storage. The storage system may be operably connected to an imaging device. The storage system may include a first storage assembly configured to obtain and store data from the imaging device. The storage system may further include a second storage assembly operably connected to the first storage assembly. And the storage system may further include a processing device configured to control communication between the first storage assembly and the second storage assembly. A write speed of the first storage assembly may exceed a write speed threshold relating to at least two parameters of the imaging device. The at least two parameters may include a first speed at which the imaging device acquires scan data, and a second speed at which the scan data is transferred to the first storage assembly.

18 Claims, 12 Drawing Sheets

(58) Field of Classification Search
CPC .... G06F 11/1448; G16H 30/20; G16H 40/20; G16H 40/67; G16H 30/00
See application file for complete search history.

(56) References Cited

U.S. PATENT DOCUMENTS

| | | | | |
|---|---|---|---|---|
| 2009/0002529 | A1* | 1/2009 | Shurboff | H04N 19/18 348/251 |
| 2010/0134654 | A1* | 6/2010 | Tsuda | H04N 1/2158 348/222.1 |
| 2015/0288847 | A1* | 10/2015 | Sakuma | H04N 1/2195 358/1.16 |

FOREIGN PATENT DOCUMENTS

| | | |
|---|---|---|
| CN | 105677587 A | 6/2016 |
| CN | 206489552 U | 9/2017 |
| CN | 108965987 A | 12/2018 |

OTHER PUBLICATIONS

Li, Ying et al., WPS Office 2012 Application Foundation Tutorial, Southeast University Press, 2013, 5 pages.

* cited by examiner

1000

Determining, based on at least one of operation information of an imaging device, usage information of the imaging device, global planning information relating to a group to which the imaging device belongs, or a storage capacity of a first storage assembly, a transfer plan for transferring at least a portion of data stored in the first storage assembly to a second storage assembly ⟵ 1010

Causing the first storage assembly to transfer, according to the transfer plan, the at least a portion of the data stored in the first storage assembly to the second storage assembly ⟵ 1020

```
┌─────────────────────────────────────────────────────────┐
│ Determining whether an available storage capacity of a first │
│ storage assembly is less than a first storage capacity       │──1110
│ threshold, the first capacity threshold relating to at least one of │
│ operation information of an imaging device, global planning │
│ information, or usage information of the imaging device     │
└─────────────────────────────────────────────────────────┘
                            │
                            ▼
┌─────────────────────────────────────────────────────────┐
│ In response to determining that the available storage capacity │
│ of the first storage assembly is less than the first storage  │──1120
│ capacity threshold, identifying, based on a first rule or a user │
│ instruction, data to be deleted or transferred from the first │
│ storage assembly                                             │
└─────────────────────────────────────────────────────────┘
                            │
                            ▼
┌─────────────────────────────────────────────────────────┐
│ Causing the first storage assembly to delete the data to be │──1130
│ deleted from the first storage assembly                     │
└─────────────────────────────────────────────────────────┘
```

FIG. 11

SYSTEMS AND METHODS FOR DATA STORAGE

CROSS-REFERENCE TO RELATED APPLICATIONS

This application claims priority of Chinese Patent Application No. 201910827536.3 filed on Sep. 3, 2019, the contents of which are incorporated herein by reference in their entirety.

TECHNICAL FIELD

The present disclosure generally relates to data storage.

BACKGROUND

A medical imaging scan may be performed using a plurality of scanning systems, such as a magnetic resonance (MR) imaging system, a computed tomography (CT) imaging system, an X-ray imaging system, a positron emission tomography (PET) imaging system, a digital radiography (DR) system, or the like, or any combination thereof. During the medical imaging scan, the scanning system can acquire a large amount of scan data at a very high speed that needs to be stored for subsequent processing.

SUMMARY

An aspect of the present disclosure relates to a storage system operably connected to an imaging device. The storage system may include a first storage assembly configured to obtain and store data from the imaging device, a second storage assembly operably connected to the first storage assembly, and a processing device configured to control communication between the first storage assembly and the second storage assembly. A write speed of the first storage assembly may exceed a write speed threshold relating to at least two parameters of the imaging device. The at least two parameters may include a first speed at which the imaging device acquires scan data, and a second speed at which the scan data is transferred to the first storage assembly.

In some embodiments, to control communication between the first storage assembly and the second storage assembly, the processing device may be configured to determine, based on at least one of operation information of the imaging device, usage information of the imaging device, global planning information relating to a group to which the imaging device belongs, and/or a storage capacity of the first storage assembly, a transfer plan for transferring at least a portion of the data stored in the first storage assembly to the second storage assembly. And the processing device may be further configured to cause the first storage assembly to transfer, according to the transfer plan, the at least a portion of the data stored in the first storage assembly to the second storage assembly.

In some embodiments, the processing device may be further configured to divide the second storage assembly into a plurality of regions based on the usage information of the imaging device.

In some embodiments, for each of the plurality of regions, a storage capacity of the region may be dynamically adjusted based on an available storage capacity of the region, the operation information of the imaging device, and/or the usage information of the imaging device.

In some embodiments, the transfer plan may include at least one of: a transfer time, an amount of data to be transferred, and/or a transfer sequence.

In some embodiments, the processing device may be further configured to determine whether an available storage capacity of the first storage assembly is less than a first storage capacity threshold. The first capacity threshold may relate to at least one of the operation information of the imaging device, the global planning information, and/or the usage information of the imaging device. The processing device may be further configured to, in response to determining that the available storage capacity of the first storage assembly is less than the first storage capacity threshold, identify, based on a first rule or a user instruction, data to be deleted or transferred from the first storage assembly, and cause the first storage assembly to delete the data to be deleted from the first storage assembly.

In some embodiments, the processing device may be further configured to determine whether an available storage capacity of the second storage assembly is less than a second storage capacity threshold. The second capacity threshold may relate to at least one of the operation information of the imaging device, the usage information of the imaging device, and/or the global planning information. The processing device may be further configured to, in response to determining that the available storage capacity of the second storage assembly is less than the second storage capacity threshold, identify, based on a second rule or a user instruction, data to be deleted or transferred from the second storage assembly, and cause the second storage assembly to delete the data to be deleted from the second storage assembly.

In some embodiments, the data stored in the second storage assembly may be encrypted data or compressed data.

In some embodiments, the first storage assembly may include at least one first storage device, and the second storage assembly may include at least one second storage device.

In some embodiments, each of the at least one first storage device may be operably connected to one or more of the at least one second storage device.

In some embodiments, a storage capacity of the first storage assembly may positively correlate with a throughput of the imaging device.

In some embodiments, a storage capacity of the first storage assembly may negatively correlate with a write speed of the second storage assembly.

In some embodiments, the write speed of the first storage assembly may be higher than a write speed of the second storage assembly.

In some embodiments, a storage capacity of the second storage assembly may be higher than a storage capacity of the first storage assembly.

Another aspect of the present disclosure relates to a storage method implemented on at least one machine operably connected to an imaging device. Each of the at least one machine may have a first storage assembly, a second storage assembly operably connected to the first storage assembly, and a processing device. The storage method may include causing the first storage assembly to obtain and store data from the imaging device, and controlling communication between the first storage assembly and the second storage assembly. A write speed of the first storage assembly may exceed a write speed threshold relating to at least two parameters of the imaging device. The at least two parameters may include a first speed at which the imaging device acquires scan data, and a second speed at which the scan data is transferred to the first storage assembly.

In some embodiments, the controlling communication between the first storage assembly and the second storage assembly may include determining, based on at least one of operation information of the imaging device, usage information of the imaging device, global planning information relating to a group to which the imaging device belongs, and/or a storage capacity of the first storage assembly, a transfer plan for transferring at least a portion of the data stored in the first storage assembly to the second storage assembly, and causing the first storage assembly to transfer, according to the transfer plan, the at least a portion of the data stored in the first storage assembly to the second storage assembly.

In some embodiments, the storage method may further include dividing the second storage assembly into a plurality of regions based on the usage information of the imaging device.

In some embodiments, the storage method may further include determining whether an available storage capacity of the first storage assembly is less than a first storage capacity threshold. The first capacity threshold may relate to at least one of the operation information of the imaging device, the global planning information, and/or the usage information of the imaging device. The storage method may further include in response to determining that the available storage capacity of the first storage assembly is less than the first storage capacity threshold, identifying, based on a first rule or a user instruction, data to be deleted or transferred from the first storage assembly, and causing the first storage assembly to delete the data to be deleted from the first storage assembly.

In some embodiments, the storage method may further include determining whether an available storage capacity of the second storage assembly is less than a second storage capacity threshold. The second capacity threshold may relate to at least one of the operation information of the imaging device, the usage information of the imaging device, and/or the global planning information. The storage method may further include in response to determining that the available storage capacity of the second storage assembly is less than the second storage capacity threshold, identifying, based on a second rule or a user instruction, data to be deleted or transferred from the second storage assembly, and causing the second storage assembly to delete the data to be deleted from the second storage assembly.

A further aspect of the present disclosure relates to a non-transitory computer readable medium. The non-transitory computer readable medium may include executable instructions that, when executed by at least one processing device, direct the at least one processing device to perform a storage method. The storage method may include causing a first storage assembly to obtain and store data from an imaging device, and controlling communication between the first storage assembly and a second storage assembly operably connected to the first storage assembly. A write speed of the first storage assembly may exceed a write speed threshold relating to at least two parameters of the imaging device. The at least two parameters may include a first speed at which the imaging device acquires scan data, and a second speed at which the scan data is transferred to the first storage assembly.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 10 is a flowchart illustrating an exemplary process for data storage according to some embodiments of the present disclosure;

FIG. 11 is a flowchart illustrating an exemplary process for storing data in a first storage assembly according to some embodiments of the present disclosure.

DETAILED DESCRIPTION

Figure 1:
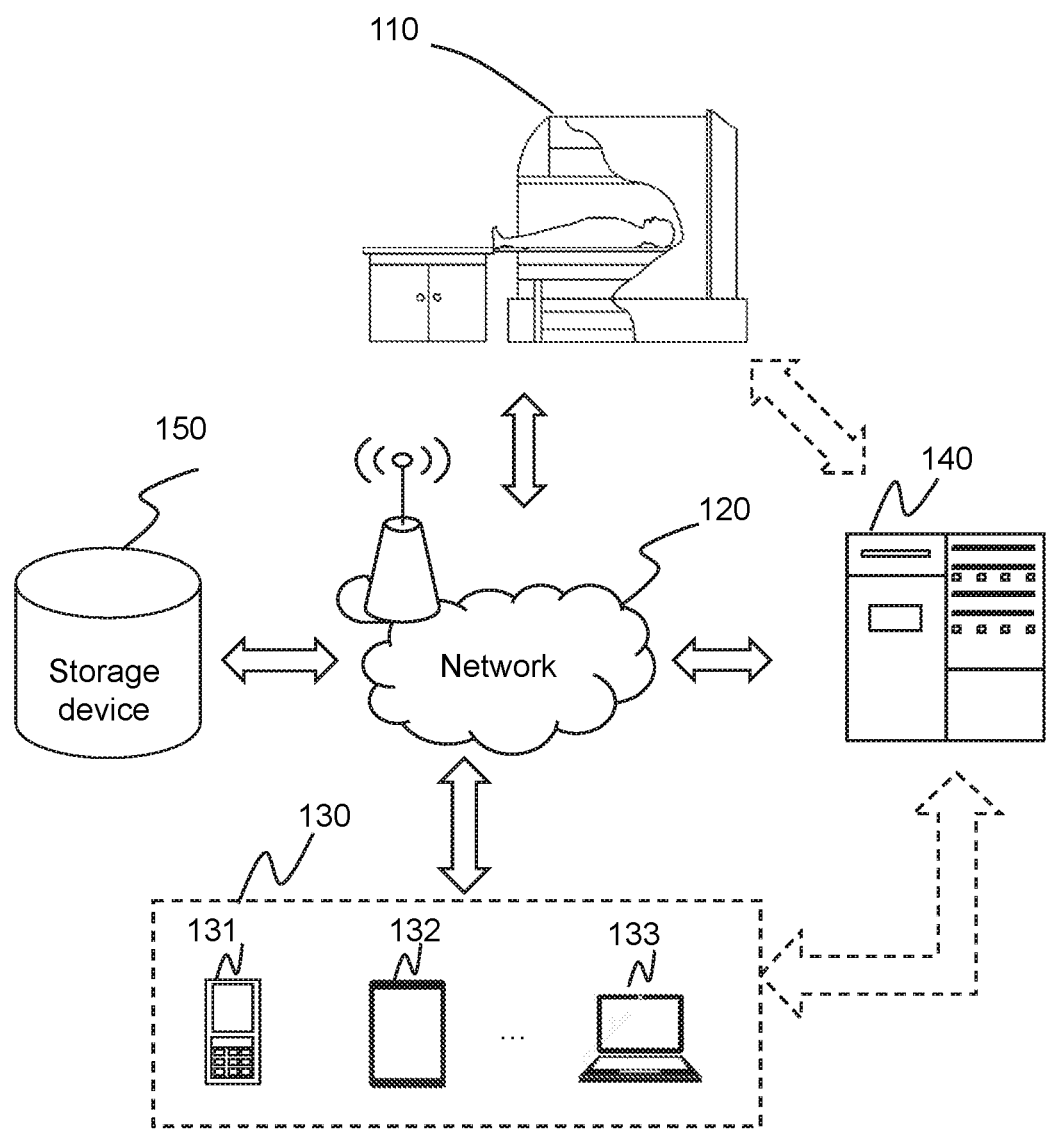
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this disclosure, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections, or assemblies of different levels in ascending order. However, the terms may be displaced by another expression if they achieve the same purpose.

Generally, the words "module," "unit," or "block" used herein refer to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for performing on computing devices (e.g., processor 210 illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to performing). Such software code may be stored, partially or fully, on a storage device of the performing computing device, for performing by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

In an imaging scan, a large amount of scan data may be generated and need to be stored substantially real-time. A data storage failure during such a scan may cause loss of scan data. Accordingly, it is desirable to prevent data storage failure from occurring during an imaging scan so as to avoid subjecting the patient to a repeated scan that takes extra time (for the patient, a user (e.g., a healthcare provider involved in the performance of the scan), the imaging device 110 that performs the scan, etc.) and/or exposes the patient to unnecessary radiation doses if radiation is involved in the scan. To this end, a storage system for storing the scan data may need to have a high storage capacity and a high write speed. For example, the storage system may include a disk array or a solid-state hard disk with a high storage capacity and a high write speed, which is expensive. Therefore, it is desirable to provide systems and methods for data storage that provides a high storage capacity and a high write speed, and at the same time is reliable and cost efficient.

The present disclosure may provide systems and methods for data storage. The storage system may be operably connected to a device or system configured to generate or otherwise have data that need to be stored. The device or system may include an imaging device (e.g., a medical imaging device). The storage system may include a first storage assembly (also referred to as "primary storage space"), a second storage assembly (also referred to as "secondary storage space") and a processing device. The first storage assembly may be configured to obtain and store data from the imaging device. The second storage assembly may be operably connected to the first storage assembly. The processing device may be configured to control communication between the first storage assembly and the second storage assembly. A write speed of the first storage assembly may exceed a write speed threshold relating to at least two parameters of the imaging device including, e.g., a first speed at which the imaging device acquires scan data, and a second speed at which the scan data is transferred to the first storage assembly. According to some embodiments of the systems and methods of the present disclosure, the first storage assembly provides a high write speed for storing data obtained from the imaging device, and the second storage assembly, while being configured with a lower write speed (and therefore more cost-efficient) than the first storage assembly, provides a high storage capacity for storing data transferred from the first storage assembly, thereby reducing the cost of data storage.

The following description is provided to facilitate better understanding of systems and/or methods for data storage. The description in connection with data relating to the imaging device described below is merely provided as an example, and not intended to limit the scope of the present disclosure. For persons having ordinary skills in the art, the systems and methods disclosed herein may be applied to any other systems and/or devices that generate data to be stored during operation.

FIG. 1 is a schematic diagram illustrating an exemplary imaging system according to some embodiments of the present disclosure. As illustrated, the imaging system 100 may include an imaging device 110, a network 120, a terminal device 130, a processing device 140, and a storage device 150. The components of the imaging system 100 may be connected in one or more of various ways. For example, the imaging device 110 may be connected to the processing device 140 through the network 120. As another example, the imaging device 110 may be connected to the processing device 140 directly (as indicated by the bi-directional arrow in dotted lines linking the imaging device 110 and the processing device 140). As a further example, the storage device 150 may be connected to the processing device 140 directly or through the network 120. As still a further example, the terminal device 130 may be connected to the processing device 140 directly (as indicated by the bi-directional arrow in dotted lines linking the terminal device 130 and the processing device 140) or through the network 120.

The imaging device 110 may scan a subject located within its detection region and generate or acquire data relating to the subject. In some embodiments, the subject may include a biological subject and/or a non-biological subject. For example, the subject may include a specific portion of a body, such as the head, the thorax, the abdomen, or the like, or a combination thereof. As another example, the subject may be a man-made composition of organic and/or inorganic matters that are with or without life. In some embodiments, the imaging system 100 may include modules and/or components for performing imaging and/or related analysis. In some embodiments, the data relating to the subject may include projection data, scan data, one or more images of the subject, etc.

In some embodiments, the imaging device 110 may be a medical imaging device for disease diagnostic or research purposes. The medical imaging device may include a single modality imaging device and/or a multi-modality imaging device. The single modality imaging device may include, for example, a magnetic resonance imaging (MRI) device, a positron emission tomography (PET) device, an emission computed tomography (ECT) device, a computed tomography (CT) imaging device, an X-ray imaging device, a molecular imaging (MI) device, a radiation therapy (RT) device, or the like, or any combination thereof. The multi-modality imaging device may include, for example, a computed tomography-magnetic resonance imaging (MRI-CT) device, a positron emission tomography-magnetic resonance imaging (PET-MRI) device, a single photon emission computed tomography-magnetic resonance imaging (SPECT-MRI) device, a digital subtraction angiography-magnetic resonance imaging (DSA-MRI) device, a computed tomography-positron emission tomography (CT-PET) device, or the like, or any combination thereof.

The network 120 may include any suitable network that can facilitate the exchange of information and/or data for the imaging system 100. In some embodiments, one or more components (e.g., the imaging device 110, the terminal device 130, the processing device 140, the storage device 150) of the imaging system 100 may communicate with one or more other components of the imaging system 100 via the network 120. For example, the processing device 140 may cause the storage device 150 to obtain data from the imaging device 110 via the network 120. As another example, the storage device 150 may include a first storage assembly and a second storage assembly. The first storage assembly may communicate with the second storage assembly via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal device 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the imaging device 110 and/or the processing device 140 may be remotely operated through the terminal device 130. In some embodiments, the imaging device 110 and/or the processing device 140 may be operated through the terminal device 130 via a wireless connection. In some embodiments, the terminal device 130 may receive information and/or instructions inputted by a user, and send the received information and/or instructions to the imaging device 110 or the processing device 140 via the network 120. In some embodiments, the terminal device 130 may receive data and/or information from the processing device 140. In some embodiments, the terminal device 130 may be part of the processing device 140. In some embodiments, the terminal device 130 may be omitted.

In some embodiments, the terminal device 130 may include a user interface. A user can provide instructions directed to the imaging system 100, manage a transfer plan, and/or manage storage assemblies via the user interface. In some embodiments, a user may query, create, modify, and/or delete the transfer plan through the user interface. For example, the user may query a current transfer plan through the user interface. Information related to the current transfer plan may be displayed to the user via the terminal device 130. The user may further adjust the transfer plan according to actual needs. In some embodiments, the user may obtain information (e.g., a total capacity, an available capacity, a transmission bandwidth, etc.) related to the storage assemblies in the imaging system 100 through the user interface. For example, the user may obtain the total capacities and the available capacities of a first storage assembly and a second storage assembly through the user interface, and determine space utilization rates of the first storage assembly and the second storage assembly. Further, the user may adjust the transfer plan for transferring at least a portion of data stored in the first storage assembly to the second storage assembly, and/or adjust available capacities of the first storage assembly and/or the second storage assembly according to the space utilization rates.

The processing device 140 may process data and/or information obtained from the imaging device 110, the terminal device 130, the storage device 150, and/or any other components associated with the imaging system 100. For example, the processing device 140 may obtain, from the imaging device 110, operation information of the imaging device 110. As another example, the processing device 140 may obtain, from the terminal device 130 or another device in or accessible by the imaging system 100, global planning information relating to a group to which the imaging device belongs. As a further example, the processing device 140 may obtain, from the first storage assembly, a storage capacity of the first storage assembly. Further, the processing device 140 may further control other components in the imaging system 100 based on the data, the information, and/or processing results. For example, the processing device 140 may determine, based on the operation information of the imaging device 110, the usage information of the imaging device 110, the global planning information, the storage capacity of the first storage assembly, etc., a transfer plan for transferring at least a portion of the data stored in the first storage assembly to the second storage assembly. The processing device 140 may further cause the first storage assembly to transfer, according to the transfer plan, the at least a portion of the data stored in the first storage assembly to the second storage assembly. In some embodiments, the processing device 140 may be a single server or a server group. The server group may be centralized or distributed. In some embodiments, the processing device 140 may be local or remote. For example, the processing device 140 may access information and/or data stored in or acquired by the imaging device 110, the terminal device 130, the storage device 150, and/or any other components associated with the imaging system 100 via the network 120. As another example, the processing device 140 may be directly connected to the imaging device 110 (as illustrated by the bidirectional arrow in dashed lines connecting the processing device 140 and the imaging device 110 in FIG. 1), the terminal device 130 (as illustrated by the bidirectional arrow in dashed lines connecting the processing device 140 and the terminal device 130 in FIG. 1), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the imaging device 110, the terminal device 130, and/or the processing device 140. For example, the storage device 150 may store scan data of a subject acquired by the imaging device 110. As another example, the storage device 150 may store historical usage information of the imaging device 110. In some embodiments, the storage device 150 may store data and/or instructions that the processing device 140 may execute or use to perform exemplary methods described in the present disclosure. For example, the storage device 150 may store instructions that the processing device 140 may execute to store the scan data acquired by the imaging device 110. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be a multi-level storage system. For example, the storage device 150 may include a first storage assembly and a second storage assembly. The first storage assembly may be configured to obtain and store data (e.g., scan data) from the imaging device 110. The second storage assembly may be operably connected to the first storage assembly. The processing device 140 may control communication between the first storage assembly and the second storage assembly. In some embodiments, a write speed of the first storage assembly may be higher than a write speed of the second storage assembly. In some embodiments, a storage capacity of the second storage assembly may be higher than a storage capacity of the first storage assembly. Merely by way of example, the first storage assembly may be or include a solid-state drive with a relatively low storage capacity and/or a relatively high write speed. The second storage assembly may be or include a mechanical hard drive with a relatively high storage capacity and/or a relatively low write speed. More descriptions regarding the first storage assembly and the second storage assembly may be found elsewhere in the present disclosure. See, e.g., FIGS. 4-7, and relevant descriptions thereof. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components (e.g., the imaging device 110, the processing device 140, the terminal device 130) of the imaging system 100. One or more components of the imaging system 100 may access the data or instructions stored in the storage device 150 via the network 120. In some embodiments, the storage device 150 may be directly connected to or communicate with one or more components (e.g., the imaging device 110, the processing device 140, the terminal device 130) of the Imaging system 100. In some embodiments, the storage device 150 may be part of the processing device 140.

In some embodiments, the imaging system 100 may further include one or more power supplies (not shown in FIG. 1) connected to one or more components (e.g., the imaging device 110, the processing device 140, the terminal device 130, the storage device 150) of the imaging system 100.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 2:
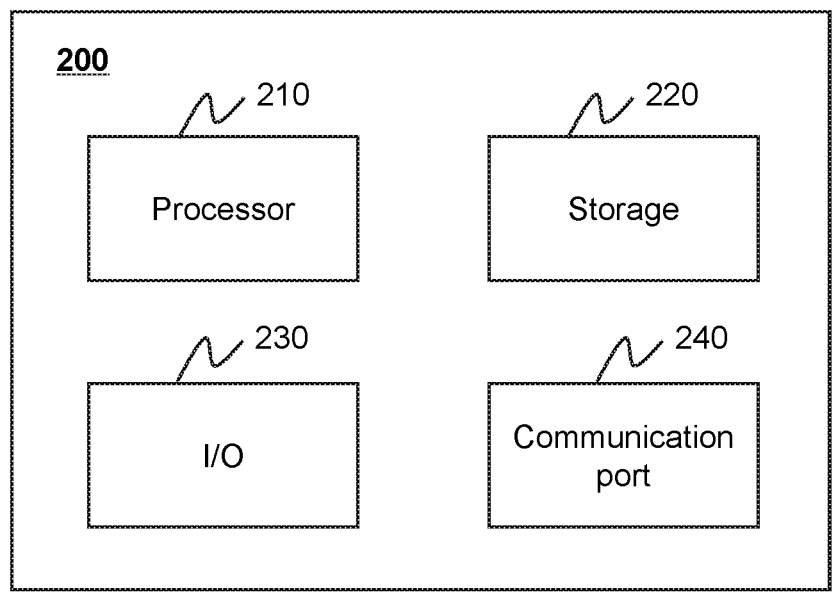
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. In some embodiments, the processing device 140 may be implemented on the computing device 200. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 210 may obtain usage information of the imaging device and divide the second storage assembly into a plurality of regions based on the usage information. In some embodiments, the processor 210 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 200. However, it should be noted that the computing device 200 in the present disclosure may also include multiple processors, and thus operations of a method that are performed by one processor as described in the present disclosure may also be jointly or separately performed by the multiple processors. For example, if in the present disclosure the processor of the computing device 200 executes both operations A and B, it should be understood that operations A and step B may also be performed by two different processors jointly or separately in the computing device 200 (e.g., a first processor executes operation A and a second processor executes operation B, or the first and second processors jointly execute operations A and B).

The storage 220 may store data/information obtained from the imaging device 110, the terminal device 130, the storage device 150, or any other component of the imaging system 100. In some embodiments, the storage 220 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for storing data obtained from the imaging device.

The I/O 230 may input or output signals, data, or information. In some embodiments, the I/O 230 may enable user interaction with the processing device 140. In some embodiments, the I/O 230 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

Merely by way of example, a user (e.g., an operator) may input data related to a subject (e.g., a patient) that is being/to be imaged/scanned through the I/O 230. The data related to the object may include identification information (e.g., a name, an age, a gender, a height, a weight, a medical history, contract information, a physical examination result). The user may also input parameters needed for the operation of the imaging device 110, such as image contrast and/or ratio, a region of interest (ROI), slice thickness, an imaging type, a scan type, a sampling type, or the like, or any combination thereof. As another example, the user can provide instruction to the imaging system 100, manage a transfer plan, and/or manage storage assemblies via the user interface. The I/O 230 may also display images generated based on imaging data and/or currently executed transfer plan.

The communication port 240 may be connected to a network (e.g., the network 120) to facilitate data communications. The communication port 240 may establish connections between the processing device 140 and the imaging device 110, the terminal device 130, the storage device 150, or any other component of the imaging system 100. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
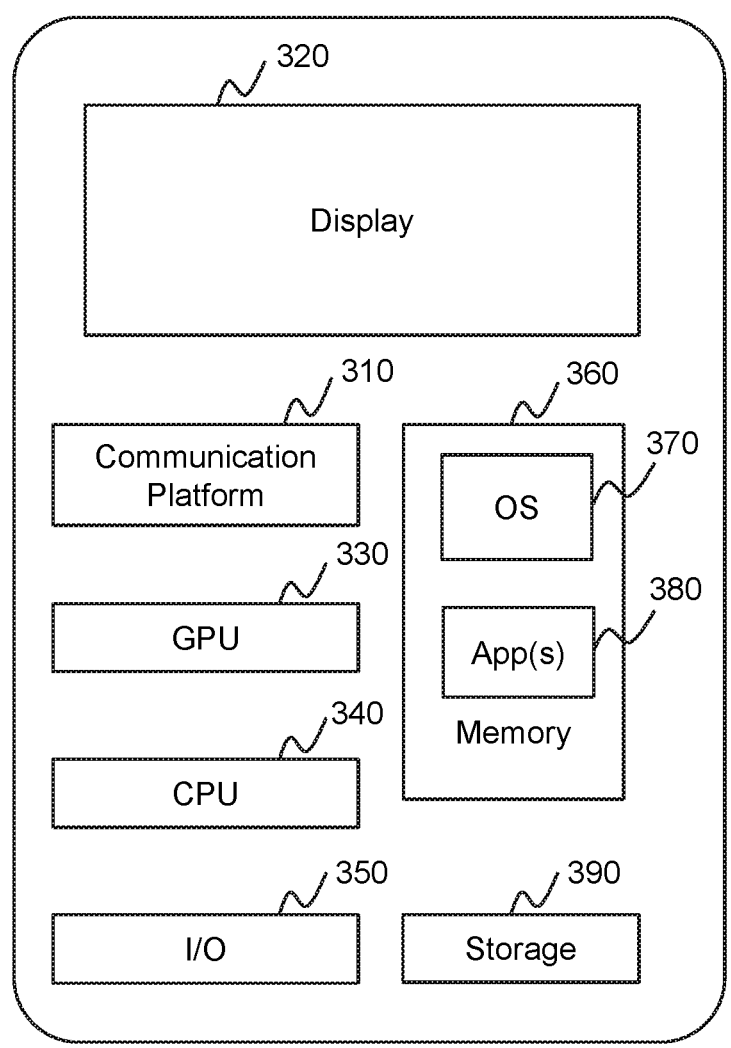
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the terminal device 130 may be implemented on the mobile device 300. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300.

In some embodiments, a mobile operating system 370 (e.g., iOS, Android, Windows Phone) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4:
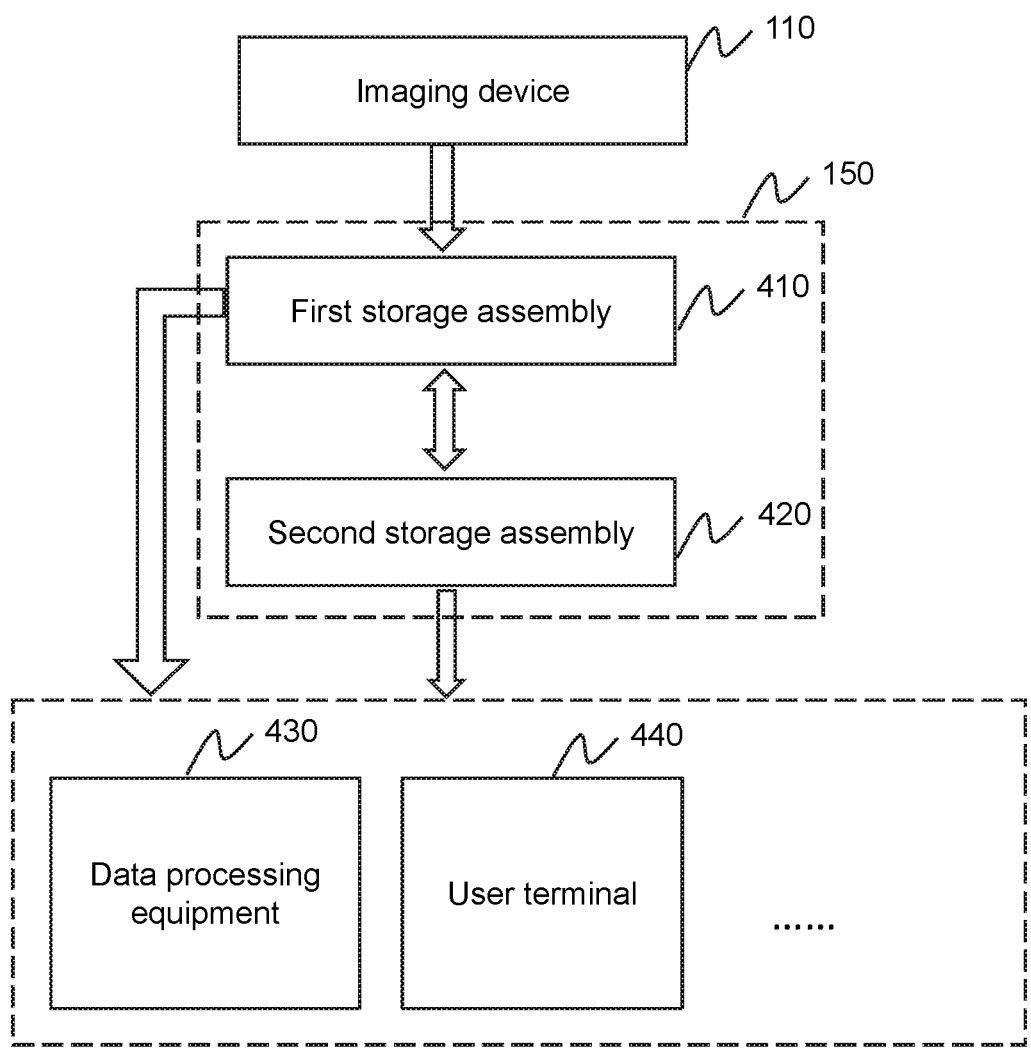
FIG. 4 is a schematic diagram illustrating exemplary components of an exemplary storage device according to some embodiments of the present disclosure.

FIG. 4 is a schematic diagram illustrating exemplary components of an exemplary storage device according to some embodiments of the present disclosure. The storage device 150 may store data and/or instructions. In some embodiments, the storage device 150 may store data obtained from a device (e.g., the imaging device 110) of the imaging system 100. In some embodiments, the storage device 150 may store data and/or instructions that a processing device (e.g., the processing device 140 illustrated in FIG. 1) may execute or use to perform methods exemplified in the present disclosure. As illustrated in FIG. 4, the storage device 150 may include a first storage assembly 410 and a second storage assembly 420.

The first storage assembly 410 may be configured to obtain and store data from the imaging device 110. In some embodiments, the imaging device 110 may include a medical imaging device (e.g., a CT imaging device). The data may include scan data acquired by a scanning component (e.g., a detector) of the medical imaging device during a scan of a subject (e.g., a patient).

In some embodiments, the first storage assembly 410 may be configured to store the scan data immediately after the scan data is acquired by the imaging device. A storage capacity of the first storage assembly 410 may satisfy a storage need of the scan data before the scan data is transferred to the second storage assembly 420. For example, the first storage assembly 410 may be able to store scan data acquired in a first time period (e.g., 1 hour, 2 hours, 4 hours, 8 hours, etc.). In some embodiments, the storage capacity of the first storage assembly 410 may positively correlate with a throughput of the imaging device 110. As used herein, the throughput of the imaging device 110 relates to one or more factors including, e.g., a count of subjects to be scanned by the imaging device 110 per unit time, the type of scan to be performed for the subject, etc. The larger the count of subjects scanned by the imaging device 110 per unit time is, the higher the throughput of the imaging device 110 may be. For example, the throughput may be represented by the count of subjects scanned by the imaging device 110 per unit time. A throughput of an imaging device that can scan 10 patients in 1 hour is higher than a throughput of an imaging device that can scan 5 patients in 1 hour, assuming that all the patients are subject to a same type of scans that produces roughly a same amount of scan data in each scan. In some embodiments, the storage capacity of the first storage assembly 410 may relate to a protocol type of the subject scanned by the imaging device 110. The protocol type refers to a scan type, such as a preliminary scan, a normal scan, an enhanced scan, etc. The protocol type of a scan may be determined by an operator of the imaging device 110 or automatically based on a scan plan. Merely by way of example, the scan data acquired in the normal scan is less than the scan data acquired in the enhanced scan. In such cases, the storage capacity of the first storage assembly 410 used for the normal scan may be lower than the storage capacity of the first storage assembly 410 used for the enhanced scan. In some embodiments, the storage capacity of the first storage assembly 410 may negatively correlate with a write speed of the second storage assembly 420. As used herein, the write speed of the second storage assembly 420 refers to a speed at which the scan data is stored in the second storage assembly 420.

In some embodiments, the scan data may be acquired at a high speed during a scan process of the imaging device 110. A low write speed of the first storage assembly 410 may cause a data storage failure of the scan data. The imaging device 110 may need to scan the subject again to acquire scan data, which may take extra time (for the subject, the user (e.g., the healthcare provider involved in the performance of the scan), the imaging device 110 that performs the scan, etc.) and cause the subject to receive additional radiation doses. Therefore, the write speed of the first storage assembly 410 may need to be determined appropriately so as to store the scan data efficiently and effectively. In some embodiments, the write speed of the first storage assembly 410 may exceed a write speed threshold relating to one or more parameters of the imaging device. Exemplary parameters may include a first speed at which the imaging device 110 acquires scan data, a second speed at which the scan data is transferred to the first storage assembly 410, etc. In some embodiments, the write speed threshold may positively correlate with the first speed and/or the second speed. The higher the first speed and/or the second speed are, the higher the write speed threshold may be. Merely by way of example, if the first speed is 80 MB/s, the second speed may be greater than or equal to the first speed, such as 100 MB/s. The write speed threshold may be larger than or equal to the second speed, such as 400 MB/s. In some embodiments, the write speed threshold may be larger than the second speed. In some embodiments, a difference between the write speed threshold and the second speed may be determined based on the amount of scan data generated per unit time (e.g., the first speed). For example, the difference may be larger than or equal to a peak value of the amount of scan data generated per unit time.

For illustration purposes, the difference between the write speed threshold and the second speed may be 20% of the second speed. For instance, if the second speed is 100 MB/s, the write speed threshold may be 120 MB/s. That is, the write speed of the first storage assembly 410 may be equal to or exceed 120 MB/s. In such cases, the first storage assembly 410 may have a relatively high write speed for storing the scan data, which may prevent data storage failure of the scan data and reduce the cost of the first storage assembly 410 by determining the write speed based on the second speed appropriately. Optionally or additionally, the second speed may be lower than the first speed. A cache mechanism may be used in the imaging device 110 to prevent loss of the scan data. For example, a cache may be provided in the imaging device 110 for a temporary storage of the scan data. In such cases, one or more storage devices with relatively low write speeds may be used in the first storage assembly, which may reduce the cost of the first storage assembly.

The second storage assembly 420 may be operably connected to the first storage assembly 410. In some embodiments, data stored in the first storage assembly 410 may be transferred to the second storage assembly 420 for storage (also referred to as "backup"). In some embodiments, the write speed of the first storage assembly 410 may be higher than a write speed of the second storage assembly 420. In some embodiments, a storage capacity of the second storage assembly 420 may be higher than the storage capacity of the first storage assembly 410. For example, the second storage assembly 420 may be able to store scan data acquired in a second time period (e.g., 5 days, 7 days, 10 days, etc.), which may need a relatively high storage capacity. In some embodiments, the second storage assembly 420 may be divided into a plurality of regions based on usage information of the imaging device 110. More descriptions regarding the plurality of regions may be found elsewhere in the present disclosure. See, e.g., FIG. 6, and relevant descriptions thereof. In some embodiments, the first storage assembly 410 may be or include a solid-state drive with a relatively low storage capacity and/or a relatively high write speed (e.g., 400 MB/s-3000 MB/s); the second storage assembly 420 may be or include a mechanical hard drive with a relatively high storage capacity and/or a relatively low write speed (e.g., 100 MB/s-200 MB/s).

Taking an imaging device that can transfer scan data to the first storage assembly 410 at a second speed of 650 MB/s as an example, 2 TB of scan data may be acquired by the imaging device in a week. To store the scan data acquired in a week, the first storage assembly 410 may be a solid-state drive with a storage capacity of 256 GB (or 512 GB) and a write speed higher than 650 MB/s (e.g., 1000 MB/s, 2000 MB/s, 3000 MB/s, etc.), and the second storage assembly 420 may be a mechanical hard drive with a storage capacity of 2 TB and a relatively low write speed (e.g., 100 MB/s, 200 MB/s, etc.). In such cases, the scan data acquired by the imaging device during a scan may be stored in the first storage assembly 410 immediately, and may be further transferred to the second storage assembly 420. The storage capacity of the second storage assembly 420 may be high enough for storing the scan data acquired in a week.

In some embodiments, the storage device 150 may exchange data and/or information with a device of or external to the imaging system 100. Exemplary devices may include the imaging device 110, a data processing equipment 430, a user terminal 440, etc. In some embodiments, the storage device 150 may obtain data and/or information from the device. For example, the first storage assembly 410 in the storage device 150 may be operably connected to the imaging device 110, and may obtain data (e.g., scan data) from the imaging device 110. Optionally or additionally, the second storage assembly 420 may also be operably connected to the imaging device 110, and may obtain data (e.g., scan data) from the imaging device 110 directly. For instance, the second storage assembly 420 may obtain data from a cache of the imaging device 110. In some embodiments, a device of or external to the imaging system 100 may obtain data and/or information from the storage device 150 (e.g., from the first storage assembly 410 and/or the second storage assembly 420). For example, the data processing equipment 430 may obtain scan data acquired in a current scan process from the first storage assembly 410 for further processing (e.g., a real-time image reconstruction). As another example, scan data acquired in a pre-scan may need to be processed as soon as possible to determine a scan plan. The data processing equipment 430 may retrieve the scan data immediately from the first storage assembly 410. As a further example, the user terminal 440 may obtain scan data acquired in the last two days from the second storage assembly 420 and display the scan data or one or more images determined based on the scan data.

It should be noted that the above description of the storage device 150 is merely provided for the purposes of illustration and not intended to limit the scope of the present disclosure. For persons having ordinary skill in the art, multiple variations and modifications may be made under the teachings of the present disclosure. However, those variations and modifications do not depart from the scope of the present disclosure. For example, one or more other components (e.g., a third storage assembly configured to store data and/or instructions that the processing device 140 may execute or use to perform exemplary methods described in the present disclosure) may be included in the storage device 150.

Figure 5:
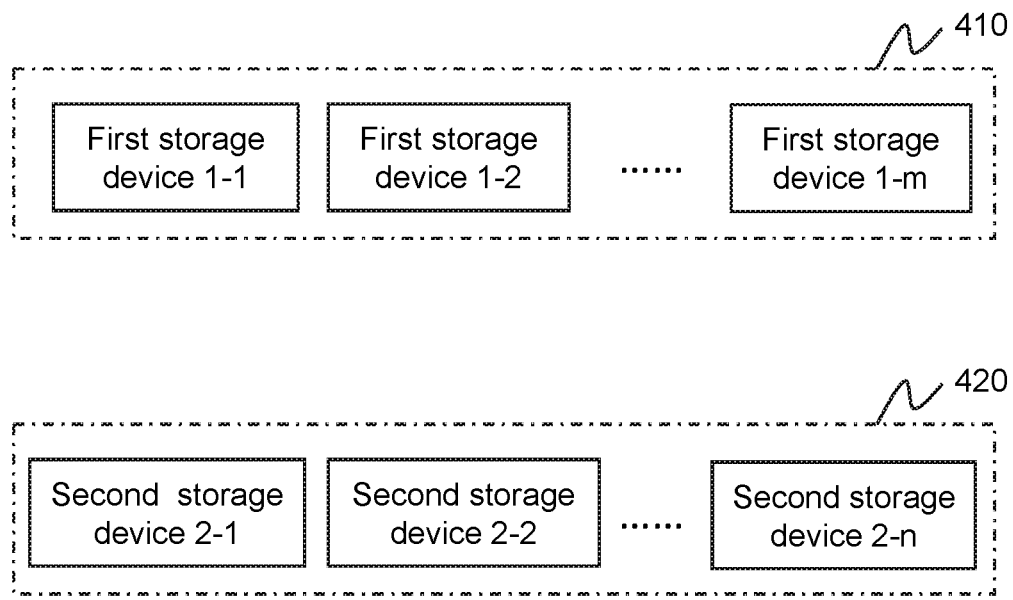
FIG. 5 is a schematic diagram illustrating an exemplary first storage assembly and an exemplary second storage assembly according to some embodiments of the present disclosure.

FIG. 5 is a schematic diagram illustrating an exemplary first storage assembly and an exemplary second storage assembly according to some embodiments of the present disclosure. In some embodiments, the first storage assembly 410 may include at least one first storage device. In some embodiments, the first storage assembly 410 may include one first storage device with a desired write speed and a desired storage capacity. In some embodiments, the first storage assembly 410 may include a plurality of first storage devices (e.g., a first storage device 1-1, a first storage device 1-2, . . . , a first storage device 1-$m$ illustrated in FIG. 5).

Merely by way of example, the first storage assembly 410 may be a redundant array of independent disks (RAID) that includes a plurality of disks (i.e., the first storage devices) each of which has the desired write speed and the desired storage capacity. As another example, the first storage assembly 410 may be an RAID that includes a plurality of disks each of which has a write speed lower than the desired write speed and a storage capacity lower than the desired storage capacity, but a combination of the plurality of disks may have the desired write speed and the desired storage capacity. As a further example, the first storage assembly 410 may include a plurality of disks each of which has a write speed with the desired write speed and a storage capacity lower than the desired storage capacity, but a combination of the plurality of disks may have the desired storage capacity. In some embodiments, each of the plurality of first storage devices in the first storage assembly 410 may store one or more types of data. For example, each of the plurality of first storage devices may store scan data of a specific subject.

In some embodiments, the second storage assembly 420 may include at least one second storage device. In some embodiments, the second storage assembly 420 may include one second storage device with a desired write speed and a desired storage capacity. In some embodiments, the second storage assembly 420 may include a plurality of second storage devices (e.g., a second storage device 2-1, a second storage device 2-2, . . . , a second storage device 2-*n* illustrated in FIG. 5). The count of the first storage device of the first storage assembly and the count of the first storage device of the first storage assembly may be the same or different. In some embodiments, each of the plurality of second storage devices in the second storage assembly 420 may store one or more types of data. For example, each of the plurality of second storage devices may store scan data acquired in a specific time period (e.g., the second storage device 2-1 may store scan data acquired on Monday, the second storage device 2-2 may store scan data acquired on Tuesday, etc.).

Figure 6:
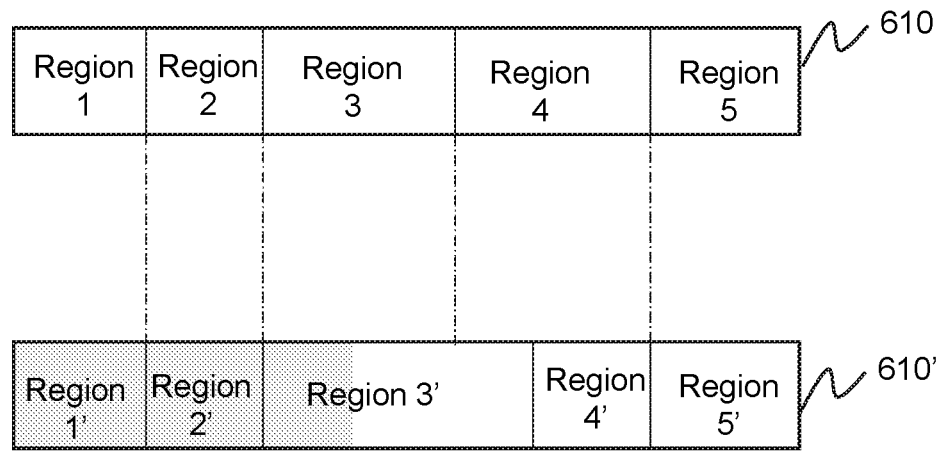
FIG. 6 is a schematic diagram illustrating exemplary regions in a second storage assembly according to some embodiments of the present disclosure.

FIG. 6 is a schematic diagram illustrating exemplary regions in a second storage assembly according to some embodiments of the present disclosure. In some embodiments, the second storage assembly may be divided into a plurality of regions (e.g., by the processing device 140) based on usage information of the imaging device. The usage information may include reservation information of the imaging device, historical usage information of the imaging device, or the like, or any combination thereof. Merely by way of example, the historical usage information of the imaging device may include types of historical scans and the amount of storage space used for storing the data acquired by the imaging device and/or information related to the historical scan data. Exemplary information related to the historical scan data may include a scanning protocol (e.g., a scan type, a scan parameter) used by the imaging device for generating historical scan data, the generation time of the historical scan data, an amount of the historical scan data, types (e.g., the age, the gender, the height, the weight, an organ of interest, etc.) of a subject corresponding to the historical scan data, or the like, or any combination thereof. The reservation information of the imaging device may include a count of subjects (e.g., patients) reserving a scan using the imaging device 110, a type (e.g., the age, the gender, the height, the weight, an organ of interest, etc.) of the subject reserving the scan, a reserved time of the scan, a reserved type of the scan, or the like, or any combination thereof.

Merely by way of example, the processing device 140 may determine types of the historical scan data, a count of the types of the historical scan data, and an amount of the historical scan data of each type based on the historical usage information of the imaging device. Further, the processing device 140 may divide the second storage assembly into the plurality of regions based on the types of historical scan data, the count of the types of the historical scan data, and the amount of the historical scan data of each type. Specifically, a count of the plurality of regions may be larger than or equal to the count of the types of the historical scan data; each of the plurality of regions may correspond to one type of historical scan data, and a storage capacity of each of the plurality of regions may be larger than or equal to the amount of the corresponding type of historical scan data.

As another example, the processing device 140 may estimate, according to the reservation information of the imaging device and/or the historical usage information of the imaging device, scan data to be acquired by the imaging device. Further, the processing device 140 may determine types of the estimated scan data, a count of the types of the estimated scan data, and an amount of the estimated scan data of each type. Furthermore, the processing device 140 may divide the second storage assembly into the plurality of regions based on the types of estimated scan data, the count of the types of the estimated scan data, and the amount of the estimated scan data of each type. Specifically, a count of the plurality of regions may be larger than or equal to the count of the types of the estimated scan data; each of the plurality of regions may correspond to one type of estimated scan data, and a storage capacity of each of the plurality of regions may be larger than or equal to the amount of the corresponding type of estimated scan data.

In some embodiments, the division of the second storage assembly may be static or fixed. For example, the count of the plurality of regions and/or the storage capacity of each of the plurality of regions may be constant. For illustration purposes, as illustrated in FIG. 6, a second storage assembly 610 may be divided in to 5 regions (e.g., region 1, region 2, region 3, region 4, region 5). In some embodiments, for each of the plurality of regions, a storage capacity of the region may be dynamically adjusted based on an available storage capacity of the region, operation information of the imaging device, the usage information of the imaging device, or the like, or any combination thereof. The operation information of the imaging device may include a type of the imaging device (e.g., a CT imaging device, an MR imaging device, a DR imaging device, a PET imaging device, etc.), a type of a subject scanned or to be scanned by the imaging device, or the throughput of the imaging device, or the like, or any combination thereof. Merely by way of example, the processing device 140 may divide the second storage assembly into a plurality of regions based on the historical usage information of the imaging device. Further, for each of the plurality of regions, the processing device 140 may dynamically adjust a storage capacity of the region based on the reservation information of the imaging device and/or the operation information of the imaging device.

For illustration purposes, as illustrated in FIG. 6, a second storage assembly 610 may be divided into 5 regions (e.g., by the processing device 140) based on the historical usage information of the imaging device. Each of the 5 regions may be used to store scan data to be acquired by the imaging device on a working day. For example, region 3 may be used to store scan data to be acquired by the imaging device on Wednesday, a storage capacity of region 3 may be equal to the amount of scan data acquired by the imaging device on last Wednesday. If a count of subject to be scanned on Wednesday in the reservation information is larger than that of last Wednesday, or the throughput of the imaging device may be increased on Wednesday, an available storage capacity of region 3 may be insufficient to store all the scan data. In such cases, the storage capacity of region 3 may need to be increased. A second storage assembly 610' with 5 adjusted regions (e.g., region 1', region 2', region 3', region 4', region 5') may be obtained.

In some embodiments, as described in connection with FIG. 5, the second storage assembly may include at least one first storage device. In some embodiments, one of the plurality of regions may be or correspond to a first storage device or a portion of the first storage device. In some embodiments, one of the plurality of regions may be or correspond to two or more first storage devices.

In some embodiments, the first storage assembly may also be divided into a plurality of regions based on the usage information of the imaging device. The first storage assembly may be divided in a similar manner as that of the second storage assembly, and the descriptions thereof are not repeated here.

Figure 7:
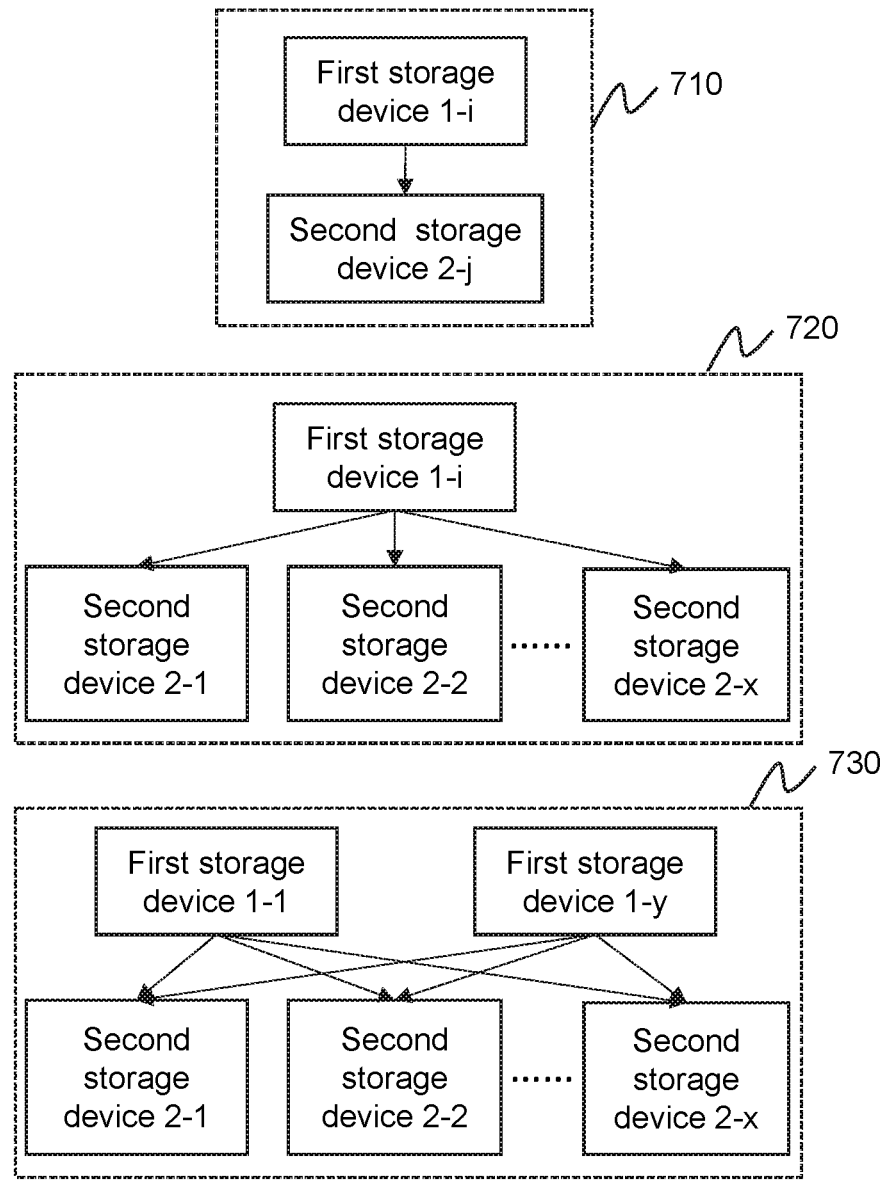
FIG. 7 is a schematic diagram illustrating exemplary relationships between a first storage assembly and a second storage assembly according to some embodiments of the present disclosure.

FIG. 7 is a schematic diagram illustrating exemplary relationships between a first storage assembly and a second storage assembly according to some embodiments of the present disclosure. In some embodiments, as described in connection with FIG. 5, the first storage assembly may include at least one first storage device, and the second storage assembly may include at least one second storage device. In some embodiments, each of the at least one first storage device may be operably connected to one or more of the at least one second storage device. For example, each of the at least one first storage device may communicate with the at least one second storage device wired (e.g., via a wire) or wirelessly (e.g., via the network 120) so as to exchange data (e.g., scan data) and/or information.

In some embodiments, each of the at least one first storage device may be operably connected to one or more of the at least one second storage device in a plurality of relationships. For example, as illustrated in FIG. 7, in a one-to-one relationship 710, one first storage device 1-*i* may be operably connected to one second storage device 2-*j*. As another example, in a one-to-many relationship 720, one first storage device 1-*i* may be operably connected to two or more second storage devices (e.g., a second storage device 2-1, a second storage device 2-2, . . . , a second storage device 2-*x*). As a further example, in a many-to-many relationship 730, at least one of the first storage devices (e.g., a first storage device 1-1, a first storage device 1-*y*) may be operably connected to two or more second storage devices (e.g., a second storage device 2-1, a second storage device 2-2, . . . , a second storage device 2-*x*), and at least one of the second storage devices (e.g., a second storage device 2-1, a second storage device 2-2, . . . , a second storage device 2-*x*) may be operably connected to two or more of the first storage devices (e.g., a first storage device 1-1, a first storage device 1-*y*).

Figure 8:
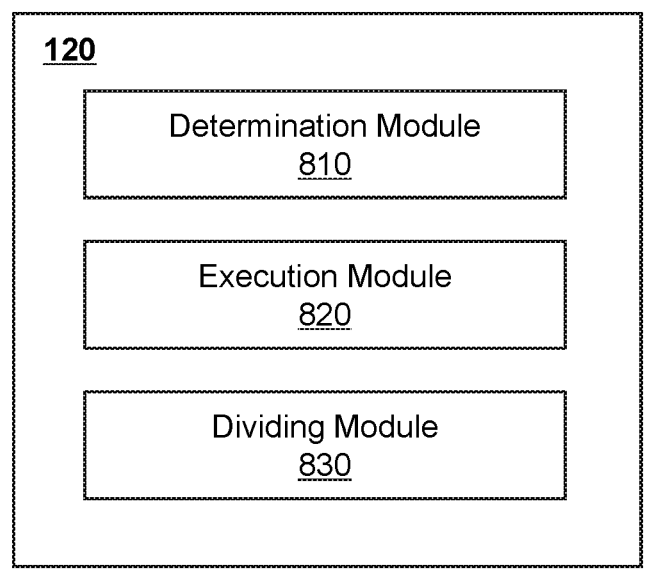
FIG. 8 is a block diagram illustrating an exemplary processing device according to some embodiments of the present disclosure.

FIG. 8 is a block diagram illustrating an exemplary processing device according to some embodiments of the present disclosure. The processing device 140 may include a determination module 810, an execution module 820, and a dividing module 830. One or more of the modules of the processing device 140 may be interconnected. The connection(s) may be wireless or wired. At least a portion of the processing device 140 may be implemented on a computing device as illustrated in FIG. 2 or a mobile device as illustrated in FIG. 3.

The determination module 810 may be configured to determine, based on operation information of an imaging device (e.g., the imaging device 110), usage information of the imaging device, global planning information relating to a group to which the imaging device belongs, a storage capacity of a first storage assembly (e.g., the first storage assembly 410), etc., a transfer plan for transferring at least a portion of the data stored in the first storage assembly to a second storage assembly (e.g., the second storage assembly 420). In some embodiments, the transfer plan may include a transfer time, an amount of data to be transferred, a transfer sequence, or the like, or a combination thereof. In some embodiments, a user may input, via a terminal device (e.g., the terminal device 130), an instruction for transferring the at least a portion of the data stored in the first storage assembly to the second storage assembly. The determination module 810 may be configured to determine the transfer plan based at least on the instruction.

The execution module 820 may be configured to cause the first storage assembly to transfer, according to the transfer plan, the at least a portion of the data stored in the first storage assembly to the second storage assembly.

In some embodiments, the determination module 810 may be further configured to determine whether an available storage capacity of the first storage assembly is less than a first storage capacity threshold. The execution module 820 may be configured to, in response to determining that the available storage capacity of the first storage assembly is less than (or equal to) the first storage capacity threshold, identify, based on a first rule or a user instruction, data to be deleted or transferred from the first storage assembly. In some embodiments, the execution module 820 may be further configured to, in response to determining that the available storage capacity of the first storage assembly is larger than (or equal to) the first storage capacity threshold, cause the first storage assembly to store the data acquired by the imaging device directly.

In some embodiments, the determination module 810 may be further configured to determine whether an available storage capacity of the second storage assembly is less than a second storage capacity threshold. The execution module 820 may be configured to, in response to determining that the available storage capacity of the second storage assembly is less than (or equal to) the second storage capacity threshold, identify, based on a second rule or a user instruction, data to be deleted or transferred from the second storage assembly. In some embodiments, the execution module 820 may be further configured to, in response to determining that the available storage capacity of the second storage assembly is larger than (or equal to) the second storage capacity threshold, cause the second storage assembly to store the data transferred from the first storage assembly directly.

The dividing module 830 may be configured to divide the second storage assembly into a plurality of regions based on the usage information of the medical imaging device. The usage information may include reservation information of the imaging device, historical usage information of the imaging device, or the like, or any combination thereof. In some embodiments, the dividing module 830 may divide the second storage assembly statically or fixedly. For example, a count of the plurality of regions and/or a storage capacity of each of the plurality of regions may be constant. In some embodiments, for each of the plurality of regions, the dividing module 830 may adjust a storage capacity of the region dynamically based on an available storage capacity of the region, operation information of the imaging device, the usage information of the imaging device, or the like, or any combination thereof. In some embodiments, the dividing module 830 may be further configured to divide the first storage assembly into a plurality of regions based on the usage information of the medical imaging device. For example, the dividing module 830 may divide the first storage assembly in a similar manner as that of the second storage assembly.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. Merely by way of example, the processing device 140 may include one or more other modules. However, those variations and modifications also fall within the scope of the present disclosure.

Figure 9:
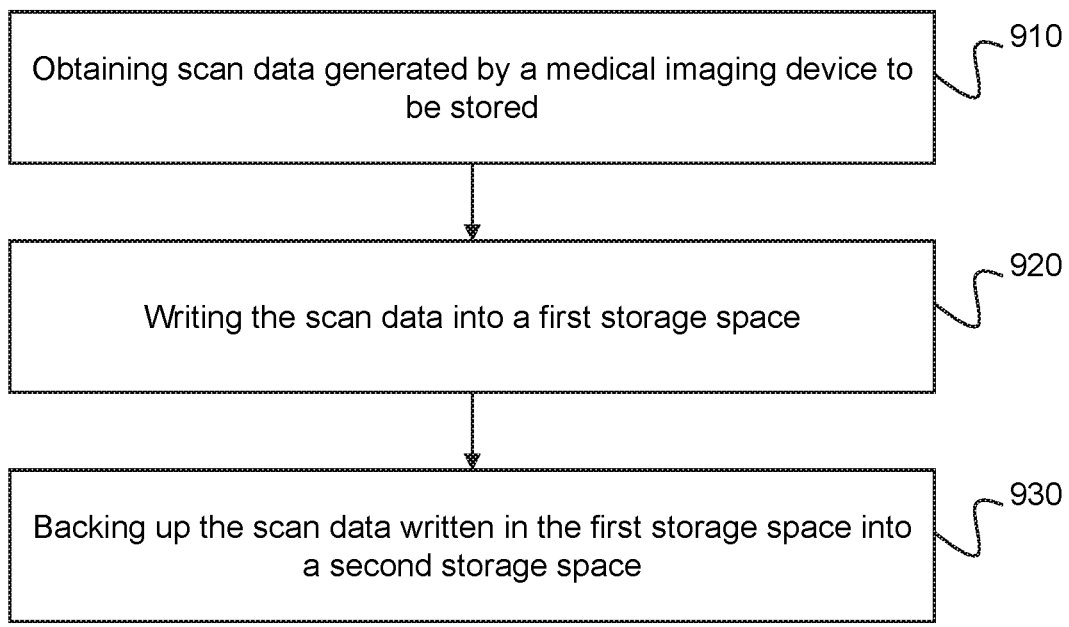
FIG. 9 is a flowchart illustrating an exemplary process for storing scan data acquired by a medical imaging device according to some embodiments of the present disclosure.

FIG. 9 is a flowchart illustrating an exemplary process for storing scan data acquired by a medical imaging device according to some embodiments of the present disclosure. In some embodiments, the process 900 may be implemented by an imaging system (e.g., the imaging system 100). In some embodiments, the imaging system may be implemented by software and/or hardware. In some embodiments, at least part of process 900 may be performed by the processing device 140 (implemented in, for example, the computing device 200 shown in FIG. 2). For example, the process 900 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, one or more modules illustrated in FIG. 8). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 910, scan data acquired by a medical imaging device to be stored may be obtained. In some embodiments, the scan data may be acquired by a medical imaging device (e.g., a CT device) by performing a scan on a subject (e.g., a patient). For example, the medical imaging device may perform the scan on the subject and acquire the scan data using a scanning component (e.g., a detector). In some embodiments, the scan data to be stored refers to scan data that has been acquired by the scanning component but has not been stored in a storage device.

In some embodiments, the medical imaging device may transmit the scan data to a computing device (e.g., the computing device 200 illustrated in FIG. 2) on which the processing device 140 is implemented. The processing device 140 may obtain the scan data through a transmission component (e.g., a slip ring) between the scanning component of the medical imaging device and the computing device. In some embodiments, the processing device 140 may obtain the scan data via a network (e.g., the network 120) or an interface. In some embodiments, 910 may be omitted so that the scan data from the medical imaging device may be written into a primary storage space as described in 920. In some embodiments, a computing device (e.g., the computing device 200 illustrated in FIG. 2) may retrieve at least a portion of the scan data from the primary storage space or a secondary storage space for image processing.

In 920, the scan data may be written into a primary storage space (also referred to as "first storage assembly"). As used herein, writing the scan data into the primary storage space refers to storing the scan data in the primary storage space. In some embodiments, the processing device 140 (e.g., the execution module 820 illustrated in FIG. 8) may cause the scan data to be store in the primary storage space in 920.

In some embodiments, as illustrated in connection with FIG. 4, the primary storage space may be configured to store the scan data immediately after the scan data is acquired by the medical imaging device. A storage capacity of the primary storage space may positively correlate with a throughput of the medical imaging device. A write speed of the primary storage space may exceed a write speed threshold relating to at least two parameters of the medical imaging device. The at least two parameters may include a first speed at which the medical imaging device acquires scan data, and a second speed at which the scan data is transferred to the primary storage space.

In some embodiments, to write the scan data to be stored into the primary storage space, a storage plan may be determined based on a determination result of whether an available storage capacity of the primary storage space satisfies a first preset condition (e.g., whether the available storage capacity of the primary storage space is less than a first storage capacity threshold). More descriptions regarding writing the scan data to be stored into the primary storage space may be found elsewhere in the present disclosure. See, e.g., FIG. 11, and relevant descriptions thereof.

In 930, the scan data written in the primary storage space may be backed up into a secondary storage space (also referred to as "second storage assembly"). As used herein, backing up scan data written in the primary storage space into the secondary storage space refers to transferring the scan data written in the primary storage space to the secondary storage space for storage. In some embodiments, the processing device 140 (e.g., the execution module 820 illustrated in FIG. 8) may cause transfer of scan data stored in the primary storage space to the secondary storage space in 930 according to a storage plan.

In some embodiments, as illustrated in connection with FIG. 4, the secondary storage space may be operably connected to the primary storage space. In some embodiments, the secondary storage space may be configured to store (also referred to as "back up") data transferred from the primary storage space. In some embodiments, the write speed of the primary storage space may be higher than a write speed of the secondary storage space. In some embodiments, a storage capacity of the secondary storage space may be higher than the storage capacity of the primary storage space. For example, the secondary storage space may be able to store scan data acquired in a second time period (e.g., 5 days, 7 days, 10 days, etc.), which may need a relatively high storage capacity than the primary storage space where scan data acquired within a relatively short period of time, a first time period (e.g., a few hours, a day), is stored before the scan data is transferred to the secondary primary space.

In some embodiments, to back up the scan data written in the primary storage space into the secondary storage space, a storage plan (also referred to as "transfer plan") may be determined based on a determination result of, e.g., whether an available storage capacity of the primary storage space satisfies a second preset condition (e.g., whether an available storage capacity of the secondary storage space is less than a second storage capacity threshold) or a transfer schedule. An exemplary transfer schedule includes that scan data acquired within one day is transferred from the primary storage space to the secondary storage space after business hours of each day.

Merely by way of example, a time interval for backing up the scan data written in the primary storage space into the secondary storage space may be determined based on a write speed of the secondary storage space. For example, if the write speed of the secondary storage space is higher than or equal to a write speed of the primary storage space, the scan data written in the primary storage space may be backed up into the secondary storage space immediately after being written into the primary storage space. As another example, if the write speed of the secondary storage space is lower than the write speed of the primary storage space, after the scan data is written into the primary storage space for a period of time, the scan data written in the primary storage space may be backed up into the secondary storage space. The time interval between when the scan data is written to the primary storage space and when the scan data starts to be transferred to the secondary storage space may relate to a difference between the write speed of the primary storage space and the secondary storage space. To finish the transfer of a certain amount of data by a specific time, the larger the difference is, the smaller the time interval may be. More descriptions regarding backing up the scan data written in the primary storage space into the secondary storage space may be found elsewhere in the present disclosure. See, e.g., FIG. 12, and relevant descriptions thereof.

According to the process for data storage illustrated in the process 900, the primary storage space provides a relatively high write speed for store scan data acquired by the medical imaging device, so as to prevent data loss and/or data storage failure, thereby preventing the subject from undergoing a repeated scan and receiving unnecessary radiation doses if radiation in involved in the scan. Further, a secondary storage space provides a relatively high storage capacity to store the scan data acquired in a certain period of time. Furthermore, the scan data may be written into the primary storage space and then backed up into the secondary storage space. On the one hand, the need for a high write speed and a high storage capacity may be satisfied by two storage components, respectively. Therefore, suitable storage devices can be selected according to the needs with a reduced cost. On the other hand, the primary storage space and the secondary storage space may be mutually redundant, thereby increasing the reliability of data storage.

It should be noted that the above description of the process 900 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, if the scan data acquired by the medical imaging device is written into the primary storage space, a feedback indicating whether the scan data is written into the primary storage space successfully may be acquired and/or sent to a terminal device (e.g., the terminal device 130) immediately. As another example, if the scan data written in the primary storage space is backed up into the secondary storage space, another feedback indicating whether the scan data written in the primary storage space is backed up into the secondary storage space successfully may be acquired and/or sent to the terminal device immediately.

FIG. 10 is a flowchart illustrating an exemplary process for data storage according to some embodiments of the present disclosure. In some embodiments, at least part of process 1000 may be performed by the processing device 140 (implemented in, for example, the computing device 200 shown in FIG. 2). For example, the process 1000 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, one or more modules illustrated in FIG. 8). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In 1010, the processing device 140 (e.g., the determination module 810) may determine, based on operation information of an imaging device (e.g., the imaging device 110), usage information of the imaging device, global planning information relating to a group to which the imaging device belongs, a storage capacity of a first storage assembly (e.g., the first storage assembly 410), etc., a transfer plan for transferring at least a portion of the data stored in the first storage assembly to a second storage assembly (e.g., the second storage assembly 420).

In some embodiments, the transfer plan may include a transfer time, an amount of data to be transferred, or a transfer sequence. For example, the processing device 140 may determine to transfer the at least a portion of the data stored in the first storage assembly immediately after it is stored in the first storage assembly, or transfer the at least a portion of the data when the storage capacity of the first storage assembly is lower than a storage threshold, or according to a schedule. As another example, the processing device 140 may determine to transfer all the data stored in the first storage assembly to the second storage assembly, or transfer a portion of the data. As a further example, the processing device 140 may determine to transfer the at least a portion of the data stored in the first storage assembly according to a time sequence when the data is acquired by the imaging device or stored in the first storage assembly, or transfer the at least a portion of the data according to usage needs of the at least a portion of the data. In some embodiments, the transfer plan may further include a transfer type. Exemplary transfer types may include a copy-and-paste, a cut-and-paste, or the like, or any combination thereof.

In some embodiments, the processing device 140 may obtain the operation information of the imaging device from one or more components of the imaging device. In some embodiments, the operation information of the imaging device may include a type of the imaging device (e.g., a CT imaging device, an MR imaging device, a DR imaging device, a PET imaging device etc.), a type (e.g., the age, the gender, the height, the weight, an organ of interest, etc.) of a subject scanned or to be scanned by the imaging device, a throughput of the imaging device, or the like, or any combination thereof. For illustration purposes, the processing device 140 may determine an amount of data to be acquired by the imaging device based on a type of the imaging device, the type of a subject scanned or to be scanned by the imaging device, the throughput of the imaging device, or the like, or any combination thereof. Further, the processing device 140 may determine a transfer plan based on the amount of data to be acquired by the imaging device and/or the storage capacity of a first storage assembly. Taking a first storage assembly with a storage capacity of 256 GB as an example, 100 GB of data has been stored in the first storage assembly. If it is estimated that 200 GB of data needs to be acquired by the imaging device at 1:00 p.m., the processing device 140 may determine to transfer at least a portion of the 100 GB of data stored in the first storage assembly before 1:00 p.m. For example, the processing device 140 may determine to transfer all the 100 GB of data stored in the first storage assembly. As another example, the processing device 140 may determine to transfer 44 GB of the data stored in the first storage assembly according to a time sequence when the data is acquired.

In some embodiments, as described in connection with FIG. 6, the usage information may include reservation information of the imaging device, historical usage information of the imaging device, or the like, or any combination thereof. Merely by way of example, the historical usage information of the imaging device may include historical scan data acquired by the imaging device and/or information related to the historical scan data. The reservation information of the imaging device may include a count of subjects (e.g., patients) reserving a scan, a type of the subject reserving a scan, a reserved time of the scan, a reserved type of the scan, or the like, or any combination thereof. For illustration purposes, the processing device 140 may estimate, according to the reservation information of the imaging device and/or the historical usage information of the imaging device, an amount of data to be acquired by the imaging device. Further, the processing device 140 may determine a transfer plan based on the amount of data to be acquired by the imaging device and/or the storage capacity of a first storage assembly. In some embodiments, the processing device 140 may obtain the usage information of the imaging device from one or more storage devices. For example, the historical usage information may be stored in a storage device (e.g., the second storage assembly in the storage device 150) of the imaging system 100. The reservation information may be stored in another storage device of a reservation system. The processing device 140 may obtain the usage information from the storage devices in the imaging system 100 and/or the reservation system. Optionally or additionally, the processing device 140 may also obtain real-time reservation information from a terminal device of a user.

In some embodiments, the global planning information relating to a group to which the imaging device 110 belongs refers to global reservation information of a subject in a group (e.g., a hospital) to which the imaging device 110 belongs. For example, the global planning information may include the global reservation information of a patient in different departments of the hospital. In some embodiments, the processing device 140 may determine a transfer plan based on the global planning information. For illustration purposes, a patient reserves a CT scan in a radiology department of a hospital, and also reserves a diagnosis meeting or treatment (e.g., a surgery) in an outpatient or impatient department of the hospital. The processing device 140 may determine a transfer time of scan data of the patient based on reservation time of the diagnosis meeting or treatment. For example, the transfer time of the scan data may be on the same day of, or one day, two days, one week, etc., before the diagnosis meeting or treatment. A doctor may obtain the scan data of the patient from the second storage assembly for further processing (e.g., for an image reconstruction, for diagnosis or treatment planning).

In some embodiments, a user may input, via a terminal device (e.g., the terminal device 130), an instruction for transferring the at least a portion of the data stored in the first storage assembly to the second storage assembly. The processing device 140 may determine the transfer plan based at least on the instruction. For example, the processing device 140 may determine to transfer the at least a portion of the data directly according to the instruction. As another example, if the instruction conflicts with the transfer plan determined by the processing device 140, the processing device 140 may generate a feedback to notify the user of the conflicts. The processing device 140 may further generate a notification to the user to prompt the user to provide further instructions on how to proceed (e.g., to proceed according to the original user instruction, to provide an adjusted user instruction, to abort the process specified by the original user instruction, to proceed according to the first rule, etc.).

In 1020, the processing device 140 (e.g., the execution module 820) may cause the first storage assembly to transfer, according to the transfer plan, the at least a portion of the data stored in the first storage assembly to the second storage assembly.

In some embodiments, the data stored in the second storage assembly may be encrypted data or compressed data. For example, the processing device 140 may perform an encryption process on the at least a portion of the data stored in the first storage assembly based on an encryption algorithm, and/or perform a compression process on the at least a portion of the data stored in the first storage assembly based on a compression algorithm. Further, the processing device 140 may cause the encrypted and/or compressed data to be stored in the second storage assembly.

In some embodiments, when the transfer plan is executed, it may be displayed on a terminal device (e.g., the terminal device 130) of a user. The user may adjust the transfer plan and/or control the transfer process via the terminal device. For example, the user may input a termination instruction via the terminal device to stop the transfer process.

It should be noted that the above description of the process 1000 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, although a process for storing data acquired by an imaging device is illustrated in process 1000, it should be understood that the method disclosed herein may also be applied to any other systems and/or devices that generate data to be stored during operation.

FIG. 11 is a flowchart illustrating an exemplary process for storing data in a first storage assembly according to some embodiments of the present disclosure. In some embodiments, at least part of process 1100 may be performed by the processing device 140 (implemented in, for example, the computing device 200 shown in FIG. 2). For example, the process 1100 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, one or more modules illustrated in FIG. 8). The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

In 1110, the processing device 140 (e.g., the determination module 810) may determine whether an available storage capacity of the first storage assembly is less than a first storage capacity threshold.

In some embodiments, the first capacity threshold may relate to the operation information of the imaging device, the global planning information, the usage information of the imaging device, or the like, or any combination thereof. For illustration purposes, the processing device 140 may estimate, according to the global planning information and/or the usage information of the imaging device, an amount of data to be acquired by the imaging device. Further, the processing device 140 may determine the first capacity threshold based on the amount of the data. For example, the first capacity threshold may be larger than or equal to the amount of the data. As another example, the global planning information and/or the usage information of the imaging device may be updated. Correspondingly, the first capacity threshold may be dynamically adjusted based on the updated global planning information and/or the updated usage information of the imaging device.

In some embodiments, the first capacity threshold may be pre-determined by a user. For example, the first capacity threshold may be 0 MB, 100 MB, 1 GB. As another example, the first capacity threshold may be 20%, 40%, etc., of the maximum storage capacity of the first storage assembly. As a further example, the available storage capacity may affect a write speed of a storage space assembly. The first capacity threshold may be larger than or equal to 20% of the of the storage capacity of the first storage assembly such that the write speed of the first storage assembly does not slow down because of a low available storage capacity.

In 1120, in response to determining that the available storage capacity of the first storage assembly is less than the first storage capacity threshold, the processing device 140 (e.g., the execution module 820) may identify, based on a first rule or a user instruction, data to be deleted or transferred from the first storage assembly.

In some embodiments, the first rule may relate to acquisition time of the data stored in the first storage assembly, a type of the data stored in the first storage assembly, the usage information of the imaging device, the global planning information, or the like, or any combination thereof. The acquisition time of the data stored in the first storage assembly refers to time when the imaging device acquires the data. The type of the data stored in the first storage assembly may relate to a type of the imaging device (e.g., a CT imaging device, an MR imaging device, a DR imaging device, etc.) and/or a type (e.g., the age, the gender, the height, the weight, an organ of interest, etc.) of the subject scanned by the imaging device. Additionally, the type of the data stored in the first storage assembly may also relate to the written time, a data size, a usage state, annotation information, etc., of the data stored in the first storage assembly. The written time refers to time when the data is stored in the first storage assembly. The usage state refers to whether the data is being used (e.g., in use, not in use). The annotation information refers to annotation (e.g., undeletable, deletable after use) determined by a user.

Merely by way of example, the first rule may be to delete (or transfer) the data stored in the first storage assembly according to a sequence of the acquisition time of the data stored in the first storage assembly after the data is transferred to the second storage assembly. As another example, the first rule may be to delete (or transfer) the data stored in the first storage assembly according to a frequency at which the data is used or retrieved. As a further example, the first rule may also include an amount of the data to be deleted or transferred from the first storage assembly. For illustration purposes, the processing device 140 may determine the amount of data to be deleted or transferred from the first storage assembly based at least on the available storage capacity of the first storage assembly and the first storage capacity threshold. Further, the processing device 140 may identify, based on the acquisition time of the data stored in the first storage assembly and the amount of data to be deleted or transferred from the first storage assembly, the data to be deleted or transferred from the first storage assembly. As still a further example, the first rule may be to delete (or transfer) the data that has been used by or transferred to another device in the group to which the imaging device belongs. For illustration purposes, the processing device 140 may determine, based on the global planning information, that a patient has reserved an examination and/or a treatment with another department of the hospital. Further, the processing device 140 may determine whether the data of the patient stored in the first storage assembly has been used in the examination and/or the treatment. Further, the processing device 140 may determine the data of the patient that has been used in the examination and/or the treatment as the identified data.

In some embodiments, a user may input, via a terminal device (e.g., the terminal device 130), a user instruction for deleting or transferring a portion of the data stored in the first storage assembly. The processing device 140 may identify, based on the user instruction, the data to be deleted or transferred from the first storage assembly. For example, the user instruction may supersede the first rule by default. The processing device 140 may identify, based on the user instruction, the data to be deleted or transferred from the first storage assembly preferentially. As another example, the processing device 140 may determine whether the user instruction conflicts with the first rule. In response to determining that the user instruction conflicts with the first rule, the processing device 140 may generate a feedback to notify the user of the conflicts. The processing device 140 may further generate a notification to the user to prompt the user to provide further instructions on how to proceed (e.g., to proceed according to the original user instruction, to provide an adjusted user instruction, to abort the process specified by the original user instruction, to proceed according to the first rule, etc.

In some embodiments, in response to determining that the available storage capacity of the first storage assembly is larger than the first storage capacity threshold, the processing device 140 may cause the first storage assembly to store the data acquired by the imaging device directly.

In 1130, the processing device 140 (e.g., the execution module 820) may cause the first storage assembly to delete the data to be deleted from the first storage assembly.

In some embodiments, the processing device 140 may cause the first storage assembly to delete the data to be deleted from the first storage assembly directly. In some embodiments, the processing device 140 may determine whether the data to be deleted from the first storage assembly has been transferred to the second storage assembly. In response to determining that the data to be deleted from the first storage assembly has been transferred to the second storage assembly, the processing device 140 may cause the first storage assembly to delete the data to be deleted from the first storage assembly. In response to determining that the data to be deleted from the first storage assembly has not been transferred to the second storage assembly, the processing device 140 may cause the first storage assembly to transfer the data to be deleted from the first storage assembly to the second storage assembly and then delete the data to be deleted from the first storage assembly. In some embodiments, the processing device 140 may overwrite the data to be deleted from the first storage assembly with new data to be stored in the first storage assembly.

According to the process illustrated in the process 1100, an available storage capacity of a first storage assembly may be adjusted before storing data such that data loss due to insufficient storage capacity can be avoided. Further, a portion of data stored in the first storage assembly may be deleted according to a first rule or a user instruction. In such cases, certain data (e.g., data acquired earlier) can be removed, and certain data (e.g., data acquired recently) can be retained, thereby improving the reliability of the certain data (e.g., the data acquired recently). Optionally or additionally, the data stored in the first storage assembly may be acquired recently by the imaging device, which has not been backed up or used. In order to further enhance the reliability of the data, the data stored in the first storage assembly may also be redundantly stored. For example, the data stored in the first storage assembly may be stored redundantly by using a RAID1.

It should be noted that the above description of the process 1100 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. Merely by way of example, the situation in which the available storage capacity of the first storage assembly is equal to the first storage capacity threshold may be handled according to a default setting of the imaging system 100 and/or a user instruction. For instance, according to a default setting of the imaging system 100, in response to determining that the available storage capacity of the first storage assembly is equal to the first storage capacity threshold, the processing device 140 may cause the first storage assembly to store the data acquired by the imaging device directly. As another example, according to a default setting of the imaging system 100, in response to determining that the available storage capacity of the first storage assembly is equal to the first storage capacity threshold, the processing device 140 may cause the first storage assembly to delete the data to be deleted from the first storage assembly, as described in 1130, before new data is written in the first storage assembly.

Figure 12:
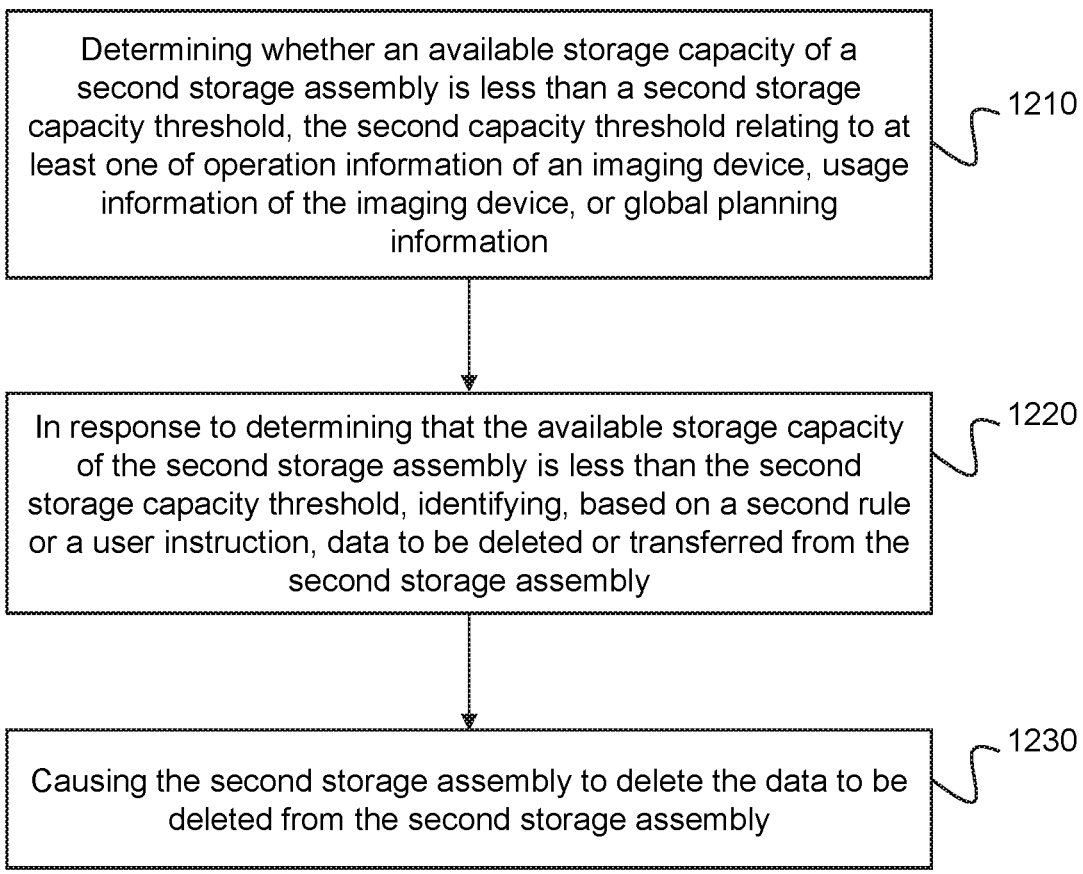
FIG. 12 is a flowchart illustrating an exemplary process for transferring data into a second storage assembly according to some embodiments of the present disclosure.

FIG. 12 is a flowchart illustrating an exemplary process for transferring data into a second storage assembly according to some embodiments of the present disclosure. In some embodiments, at least part of process 1200 may be performed by the processing device 140 (implemented in, for example, the computing device 200 shown in FIG. 2). For example, the process 1200 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, one or more modules illustrated in FIG. 8). The operations of the illustrated process presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting.

In 1210, the processing device 140 (e.g., the determination module 810) may determine whether an available storage capacity of the second storage assembly is less than a second storage capacity threshold.

In some embodiments, the second capacity threshold may relate to the operation information of the imaging device, the usage information of the imaging device, the global planning information, or the like, or any combination thereof. In some embodiments, the second capacity threshold may be pre-determined by a user. For example, the second capacity threshold may be 0 MB, 100 MB, 1 GB, etc. In some embodiments, the second capacity threshold may be dynamically adjusted according to an amount of data to be transferred from the first storage assembly to the second storage assembly. In some embodiments, the second capacity threshold may be dynamically adjusted according to an amount of data to be transferred into the second storage assembly.

In some embodiments, operation 1210 may be performed in a similar manner as operation 1110 as described in connection with FIG. 11, the descriptions of which are not repeated here.

In 1220, in response to determining that the available storage capacity of the second storage assembly is less than the second storage capacity threshold, the processing device 140 (e.g., the determination module 810) may identify, based on a second rule or a user instruction, data to be deleted or transferred from the second storage assembly.

In some embodiments, the second rule may relate to acquisition time of the data stored in the second storage assembly, a type of the data stored in the second storage assembly, the usage information of the imaging device, the global planning information, or the like, or any combination thereof. The acquisition time of the data stored in the second storage assembly refers to time when the imaging device acquires the data. The type of the data stored in the second storage assembly may relate to a type of the imaging device and/or a type of the subject scanned by the imaging device. Additionally, the type of the data stored in the second storage assembly may also relate to written time, a data size, a usage state, annotation information, etc. of the data stored in the second storage assembly.

Merely by way of example, the second rule may be to delete (or transfer) the data stored in the second storage assembly according to a sequence of the acquisition time of the data stored in the second storage assembly. As another example, the second rule may include an amount of the data to be deleted or transferred from the second storage assembly. As a further example, the second rule may be to delete (or transfer) the data that has been used by or transferred to another device in the group to which the imaging device belongs.

In some embodiments, a user may input, via a terminal device (e.g., the terminal device 130), a user instruction for deleting or transferring a portion of the data stored in the second storage assembly. The processing device 140 may identify, based on the user instruction, the data to be deleted or transferred from the second storage assembly.

In some embodiments, in response to determining that the available storage capacity of the second storage assembly is larger than the second storage capacity threshold, the processing device 140 may cause the second storage assembly to store the data transferred from the first storage assembly directly.

In some embodiments, operation 1220 may be performed in a similar manner as operation 1120 as described in connection with FIG. 11.

In 1230, the processing device 140 (e.g., the execution module 820) may cause the second storage assembly to delete the data to be deleted from the second storage assembly.

In some embodiments, the processing device 140 may cause the second storage assembly to delete the data to be deleted from the second storage assembly directly. In some embodiments, the processing device 140 may cause the second storage assembly to transfer the data to be deleted from the second storage assembly to other processing devices or storage devices. In some embodiments, the processing device 140 may overwrite the data to be deleted from the second storage assembly with the data transferred from the first storage assembly.

According to the process illustrated in the process 1200, an available storage capacity of a second storage assembly may be adjusted before transferring data such that data storage failure in the second storage assembly due to insufficient storage capacity can be avoided. Further, a portion of data stored in the second storage assembly may be deleted according to a second rule or a user instruction. In such cases, certain data (e.g., data acquired earlier) can be removed, and certain data (e.g., data acquired recently) can be retained, thereby improving the reliability of the certain data (e.g., the data acquired recently).

It should be noted that the above description of the process 1200 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. Merely by way of example, the situation in which the available storage capacity of the second storage assembly is equal to the second storage capacity threshold may be handled according to a default setting of the imaging system 100 and/or a user instruction. For instance, according to a default setting of the imaging system 100, in response to determining that the available storage capacity of the second storage assembly is equal to the second storage capacity threshold, the processing device 140 may cause the second storage assembly to store the data transferred from the first storage assembly directly. As another example, according to a default setting of the imaging system 100, in response to determining that the available storage capacity of the second storage assembly is equal to the second storage capacity threshold, the processing device 140 may cause the second storage assembly to delete the data to be deleted from the second storage assembly, as described in 1230, before new data is transferred into the second storage assembly.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction performing system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A storage system operably connected to an imaging device, comprising:
   a first storage assembly configured to obtain and store data from the imaging device, wherein the first storage assembly is able to store data acquired with a first time period;
   a second storage assembly operably connected to the first storage assembly, wherein the second storage assembly is able to store data acquired within a second time period, the second time period being larger than the first time period, wherein the second storage assembly is divided into a plurality of regions based on at least one of types of historical scan data, a count of the types of the historical scan data, or an amount of the historical scan data of each type, or based on at least one of types of estimated scan data, a count of the types of the estimated scan data, or an amount of the estimated scan data of each type, wherein
   for each of the plurality of regions, a storage capacity of the region is dynamically adjusted based on at least one of a type of the imaging device, a type of a subject scanned by the imaging device, or a throughput of the imaging device; and
   a processing device configured to control communication between the first storage assembly and the second storage assembly, wherein the processing device is further configured to:
   determine an amount of data to be acquired by the imaging device based on at least one of the type of the imaging device, the type of the subject scanned by the imaging device, or the throughput of the imaging device, or based on at least one of reservation information of the imaging device or historical usage information of the imaging device; and
   determine a transfer plan for transferring at least a portion of the data stored in the first storage assembly to the second storage assembly based on the amount of data to be acquired by the imaging device, wherein
   a write speed of the first storage assembly exceeds a write speed threshold relating to at least two parameters of the imaging device, the at least two parameters including a first speed at which the imaging device acquires scan data and a second speed at which the scan data is transferred to the first storage assembly.

2. The storage system of claim 1, wherein
for each of the plurality of regions, the storage capacity of the region is dynamically adjusted based on an available storage capacity of the region, operation information of the imaging device, or the usage information of the imaging device.

3. The storage system of claim 1, wherein the transfer plan includes at least one of: a transfer time, an amount of data to be transferred, or a transfer sequence.

4. The storage system of claim 1, wherein the processing device is further configured to:
   determine whether an available storage capacity of the first storage assembly is less than a first storage capacity threshold, the first capacity threshold relating to at least one of the operation information of the imaging device, the global planning information, or the usage information of the imaging device;
   in response to determining that the available storage capacity of the first storage assembly is less than the first storage capacity threshold, identify, based on a first rule or a user instruction, data to be deleted or transferred from the first storage assembly; and
   cause the first storage assembly to delete the data to be deleted or to transfer the data to be transferred from the first storage assembly.

5. The storage system of claim 1, wherein the processing device is further configured to:
   determine whether an available storage capacity of the second storage assembly is less than a second storage capacity threshold, the second capacity threshold relating to at least one of the operation information of the imaging device, the usage information of the imaging device, or the global planning information;
   in response to determining that the available storage capacity of the second storage assembly is less than the second storage capacity threshold, identify, based on a second rule or a user instruction, data to be deleted or transferred from the second storage assembly; and cause the second storage assembly to delete the data to be deleted or to transfer data to be transferred from the second storage assembly.

6. The storage system of claim 1, wherein the data stored in the second storage assembly is encrypted data or compressed data.

7. The storage system of claim 1, wherein
the first storage assembly includes at least one first storage device, and
the second storage assembly includes at least one second storage device.

8. The storage system of claim 7, wherein each of the at least one first storage device is operably connected to one or more of the at least one second storage device.

9. The storage system of claim 1, wherein
a storage capacity of the first storage assembly positively correlates with a throughput of the imaging device.

10. The storage system of claim 1, wherein
a storage capacity of the first storage assembly negatively correlates with a write speed of the second storage assembly.

11. The storage system of claim 1, wherein
the write speed of the first storage assembly is higher than a write speed of the second storage assembly.

12. The storage system of claim 1, wherein
a storage capacity of the second storage assembly is higher than a storage capacity of the first storage assembly.

13. The storage system of claim 1, wherein a difference between the write speed threshold and the second speed is larger than or equal to a peak value of the first speed.

14. The storage system of claim 1, wherein
the first storage assembly is configured to store the data immediately after the data is acquired by the imaging device; and
the second storage assembly is configured to backup data stored in the first storage assembly when no scan is executed by the imaging device.

15. The storage system of claim 1, wherein
a count of the plurality of regions is larger than or equal to the count of the types of the historical scan data;
each of the plurality of regions corresponds to one type of historical scan data; and
a storage capacity of each of the plurality of regions is larger than or equal to the amount of the corresponding type of historical scan data.

16. The storage system of claim 1, wherein
a count of the plurality of regions is larger than or equal to the count of the types of the estimated scan data;
each of the plurality of regions corresponds to one type of estimated scan data; and
a storage capacity of each of the plurality of regions is larger than or equal to the amount of the corresponding type of estimated scan data.

17. A storage method implemented on at least one machine operably connected to an imaging device, each of the at least one machine having a first storage assembly, a second storage assembly operably connected to the first storage assembly, and a processing device, the storage method comprising:
causing the first storage assembly to obtain and store data from the imaging device, wherein the first storage assembly is able to store data acquired with a first time period; and
controlling communication between the first storage assembly and the second storage assembly, wherein the second storage assembly is able to store data acquired within a second time period, the second time period being larger than the first time period, wherein the second storage assembly is divided into a plurality of regions based on at least one of types of historical scan data, a count of the types of the historical scan data, or an amount of the historical scan data of each type, or based on at least one of types of estimated scan data, a count of the types of the estimated scan data, or an amount of the estimated scan data of each type, wherein
for each of the plurality of regions, a storage capacity of the region is dynamically adjusted based on at least one of a type of the imaging device, a type of a subject scanned by the imaging device, or a throughput of the imaging device;
determining an amount of data to be acquired by the imaging device based on at least one of the type of the imaging device, the type of the subject scanned by the imaging device, or the throughput of the imaging device, or based on at least one of reservation information of the imaging device or historical usage information of the imaging device; and
determining a transfer plan for transferring at least a portion of the data stored in the first storage assembly to the second storage assembly based on the amount of data to be acquired by the imaging device, wherein
a write speed of the first storage assembly exceeds a write speed threshold relating to at least two parameters of the imaging device, the at least two parameters including a first speed at which the imaging device acquires scan data, and a second speed at which the scan data is transferred to the first storage assembly.

18. A non-transitory computer readable medium, comprising executable instructions that, when executed by at least one processing device, direct the at least one processing device to perform a storage method, the storage method comprising:
causing a first storage assembly to obtain and store data from an imaging device, wherein the first storage assembly is able to store data acquired with a first time period; and
controlling communication between the first storage assembly and a second storage assembly operably connected to the first storage assembly, wherein the second storage assembly is able to store data acquired within a second time period, the second time period being larger than the first time period, wherein the second storage assembly is divided into a plurality of regions based on at least one of types of historical scan data, a count of the types of the historical scan data, or an amount of the historical scan data of each type, or based on at least one of types of estimated scan data, a count of the types of the estimated scan data, or an amount of the estimated scan data of each type, wherein
for each of the plurality of regions, a storage capacity of the region is dynamically adjusted based on at least one of a type of the imaging device, a type of a subject scanned by the imaging device, or a throughput of the imaging device;
determining an amount of data to be acquired by the imaging device based on at least one of the type of the imaging device, the type of the subject scanned by the imaging device, or the throughput of the imaging device, or based on at least one of reservation information of the imaging device or historical usage information of the imaging device; and
determining a transfer plan for transferring at least a portion of the data stored in the first storage assembly to the second storage assembly based on the amount of data to be acquired by the imaging device, wherein a write speed of the first storage assembly exceeds a write speed threshold relating to at least two parameters of the imaging device, the at least two parameters including a first speed at which the imaging device acquires scan data, and a second speed at which the scan data is transferred to the first storage assembly.

* * * * *